United States Patent
Holstein et al.

(10) Patent No.: US 10,658,996 B2
(45) Date of Patent: May 19, 2020

(54) RENDERING WIDEBAND ULTRASONIC SIGNALS AUDIBLE

(71) Applicant: SONOTEC Ultraschallsensorik Halle GmbH, Halle (Saale) (DE)

(72) Inventors: Peter Holstein, Taucha (DE); Sebastian Uziel, Ilmenau (DE); David Januszko, Ilmenau (DE); Andreas Tharandt, Leipzig (DE); Ronald John, Halle (DE); Nicki Bader, Halle (DE)

(73) Assignee: SONOTEC Ultraschallsensorik Halle GmbH, Halle (Saale) (DE)

( * ) Notice: Subject to any disclaimer, the term of this patent is extended or adjusted under 35 U.S.C. 154(b) by 409 days.

(21) Appl. No.: 15/455,336

(22) Filed: Mar. 10, 2017

(65) Prior Publication Data

US 2017/0264255 A1     Sep. 14, 2017

(30) Foreign Application Priority Data

Mar. 11, 2016     (DE) ................ 10 2016 104 533

(51) Int. Cl.
| | | |
|---|---|---|
| H03G 7/00 | (2006.01) |
| H03G 3/00 | (2006.01) |
| H03G 3/20 | (2006.01) |
| A61B 8/00 | (2006.01) |
| G10K 15/00 | (2006.01) |
| G10K 11/18 | (2006.01) |
| G01H 3/08 | (2006.01) |

(52) U.S. Cl.
CPC ............... *H03G 7/007* (2013.01); *A61B 8/00* (2013.01); *G10K 11/18* (2013.01); *G10K 15/00* (2013.01); *H03G 3/002* (2013.01); *H03G 3/20* (2013.01); *G01H 3/08* (2013.01)

(58) Field of Classification Search
CPC .......... H03G 3/002; H03G 3/20; H03G 7/007; G10K 15/00; G10K 11/18; A61B 8/00; G01H 3/08
USPC .......................................... 367/135
See application file for complete search history.

(56) References Cited

FOREIGN PATENT DOCUMENTS

| | | |
|---|---|---|
| JP | 2010-002367 A | 1/2010 |
| WO | WO 2006/025798 A1 | 3/2006 |

OTHER PUBLICATIONS

English translation of Description section of Patents Application 2008-162971, corresponding to JP 2010-002367, downloaded May 8, 2019 from https://www.j-platpat.inpit.go.jp/h0101, 11 pages. (Year: 2008).*

(Continued)

*Primary Examiner* — Daniel L Murphy
(74) *Attorney, Agent, or Firm* — Olson & Cepuritis, Ltd.

(57) ABSTRACT

The invention relates to a method for rendering ultrasonic signals audible that is characterized in that the temporal dynamic range of the ultrasonic signal is maintained. The amplitude profile of the ultrasonic signal picked up in the time domain remains unaltered. The frequency shift from the ultrasonic range to the audible range is possible up to a factor of 32 using the present invention.

8 Claims, 4 Drawing Sheets

(56) References Cited

OTHER PUBLICATIONS

Petterson; Electronic AB, Ultrasound Detector D 230; Nov. 24, 2014.
Runkel, V.; Vergleich gangiger Hardware fur die Feldermauserfassung, Oct. 26, 2010, ecoObs GmbH.
Smagowska, B.; Ultrasonic Noise Sources in a Work Environment, Archives of Acoustics, vol. 38, No. 2, 2013, pp. 169-176.
Osterreichisches Normungsinstitut: Schallschutz und Raumakustik im Hochbau Teil 2: Anforderungen an den Schallschutz; Dec. 1, 2002.

* cited by examiner (a)

(b)

(a)

(b)

(c)

(a)

(b)

(c)

RENDERING WIDEBAND ULTRASONIC SIGNALS AUDIBLE

CROSS-REFERENCE TO RELATED APPLICATION

This application claims priority of German Patent Application No. 10 2016 104 533.0, filed Mar. 11, 2016, incorporated herein by reference.

FIELD OF THE INVENTION

The invention relates to a method for rendering ultrasonic signals audible that is characterized in that the temporal dynamic range of the ultrasonic signal is maintained. The amplitude profile of the ultrasonic signal picked up in the time domain remains unaltered. The transformation from the ultrasonic range to the audible range is possible up to a factor of 32 using the present invention.

PRIOR ART

Ultrasound is increasingly used for technical diagnosis. The ultrasound can be produced in a wide variety of ways in this case. Mechanical friction, pulsed excitation, material deformation, flow turbulence, cracking processes and electrical discharges produce ultrasound. This ultrasound can be regarded as a source of information about the producing medium. In the industrial sector, ultrasound is therefore used in maintenance, for example (machine diagnosis, looking for compressed air leaks, finding electrical discharges, inter alia). Ultrasound can also be produced specifically using suitable sources (loudspeakers, piezoelectric sources, dog whistles, inter alia). These are used wherever a deterministic source is needed. An example is checking the imperviousness of cabins or other volumes or the general issue of acoustic imperviousness.

A further type of ultrasonic sources can be found in the biological sector. Bats (order Chiroptera) and others actively produce ultrasound in order to orient themselves in space or to locate objects. The invention can also be applied to the biological sector.

The human ear allows high and low sounds in the sonic image to be identified at the same time. This produces the capability for acoustic orientation, communication and threat detection. This is also the basis for speech and listening to and anticipating music. This capability of the human being can be used to assess the properties of a sound source. This is not possible for sound sources whose frequencies are in the ultrasonic range (frequencies from approximately 16 kHz to 1 GHz), since ultrasound cannot be perceived by the human ear. Assessment of ultrasonic signals by the human ear and hence on the basis of the experience of trained collaborators is of great technical significance, since this allows simple assessment of the characteristics of sound sources to be performed. In this way, it would be possible to obtain an overview of the ultrasonic spectrum.

It is accordingly of great technical benefit to convert ultrasonic signals into audible frequencies. In so doing, however, the characteristics of the ultrasonic signal need to be maintained so as not to corrupt the evaluation of the signals. Established methods for rendering ultrasonic signals audible simplify the signal content of ultrasonic signals to such an extent that the spectral content of the original signal and of the modulation thereof is lost, however. Therefore, these methods can be used only in simple cases and deliver statements that are only limited and not always correct.

Eliminating these disadvantages of the prior art is the object of the present invention. A method is provided that allows transformation of an ultrasonic signal into the audible range without the temporal dynamic range of said ultrasonic signal being lost.

SUMMARY OF THE INVENTION

The invention relates to a method for rendering ultrasonic signals audible that is characterized in that the temporal dynamic range of the ultrasonic signal is maintained. That is to say that the amplitude profile of the ultrasonic signal picked up in the time domain remains unaltered.

Sound and hence also ultrasound propagates as a progressive disturbance of the local density of the air in the room. This change in the local density can be measured in the form of the sound pressure p as a function of time. A further sound field variable that describes a sound field is the sound pressure level.

The sound pressure level is computed as follows $$L_p = 10 lg\left(\frac{\langle p(t)^2 \rangle}{p_0^2}\right)$$

with $p_0$ as a suitable reference value. Usually, $p_0 = 20\ \mu Pa$ is used therefor in acoustics. The signal picked up in the time domain can be converted into the frequency domain by a Fourier transformation.

For human beings, the eardrum of the ear performs the function of a sound detector. However, human beings are only capable of perceiving sounds in a limited range of frequency and sound pressure level. This range is defined by what is known as the auditory field. For human beings, it is accordingly only possible to perceive changes of amplitude in the time signal that are within the auditory field of human beings. The auditory field of human beings will define the audible range within the scope of this application.

The method according to the invention preferably involves only components of the ultrasonic signal whose amplitude variation is in the audible range of human beings being processed. Amplitude variations that are in the inaudible range of human beings are, by contrast, preferably not considered.

The method according to the invention therefore allows ultrasonic signals that are caused by a technical or biological process to be represented in the range audible to human beings. The transformation of the ultrasonic signals into the audible range can be performed substantially in real time in this case. Thus, reproduction of the ultrasonic signals in the audible range is possible substantially in sync with the process causing the ultrasonic signals.

The ultrasonic signals are picked up by suitable microphones or sensors and converted into electrical signals. As a result, all of the physical information that the acoustic signal contains is maintained for the further processing. The signals are digitized and, by means of suitable transformations, processed such that after the processing they are in a frequency range that allows them to be listened to through a loudspeaker or headphones. After they have passed through the whole signal processing chain, the data are available in the time domain and can be rendered audible in the manner of ordinary acoustic signals.

The time signal can be used for further processing operations such as the computation of level values, spectra, wavelets, envelopes, spectrograms, kurtograms, inter alia.

DETAILED DESCRIPTION OF THE INVENTION

In a preferred embodiment of the method according to the invention, the ultrasonic signals have their frequencies compressed. That is to say that the method according to the invention is used to produce compressed acoustic data. The compression of the acoustic data transforms them into the audible range. That is to say that the frequency of the signal is compressed. A suitable choice of compression factor ensures that the amplitude profile is maintained. The compression factor is chosen such that the spectral range to be considered falls completely into the audible range. An exemplary embodiment of the ultrasonic range from 20 to 100 kHz is the choice of a compression factor of 32.

In an embodiment of the method according to the invention, the acoustic signals rendered audible are not reproduced but rather are stored. In this case, the compression of the acoustic data reduces the amount of memory in comparison with the original acoustic data substantially. This is particularly useful for the long-term recording of acoustic data, in particular.

According to the invention, the ultrasonic signal is detected using a suitable microphone, such as a wideband ultrasonic microphone, for example, or a suitable sensor, such as a wideband structure-borne sound sensor, for example.

In an embodiment of the method according to the invention,
- an ultrasonic signal is detected using a suitable microphone or a suitable sensor,
- the analogue signal is converted into a digital signal using an A/D converter,
- the digital signal is transferred to a computation unit, and this may be a Field Programmable Gate Array (FPGA), for example,
- a continuous data stream is transferred from the computation unit to a D/A converter, and
- the acoustic signal obtained is output.

The ultrasonic signal is sampled continuously at a suitable sampling rate (e.g. 250 kHz). The analogue signal is converted into a digital signal in an analogue/digital converter (A/D converter). In this case, acoustic components of the detected signal that are in the audible range are filtered from the signal by a high-pass filter (e.g. with a cut-off frequency of 20 kHz). An anti-aliasing filter ensures that no higher spurious frequencies are convoluted back into the signal that is to be rendered audible. A/D converters having a resolution of 16 or 24 bits, for example, are suitable for the method according to the invention.

The signal is subsequently transferred to a computation unit. The computation unit implements a block-by-block signal breakdown, and subsequently transformation of the time signal into the frequency domain is performed on a block-by-block basis. This transformation into the frequency domain is implemented using a Fourier transformation. Subsequently, the frequency signal is back-transformed into a time signal using a Fourier back-transformation. Subsequently, synthesis of the time signals transformed block by block to produce a time signal is performed. The new time signal has a lower sampling rate in comparison with the output signal. The digital transformed time signal is transferred in the form of a continuous data stream at a lower sampling rate than the original signal to a digital-to-analogue converter (D/A converter) that converts the digital time signal into an analogue time signal. The transformed acoustic signal can then be output.

In an embodiment of the invention, a field programmable gate array (FPGA) is used as the computation unit. An FPGA is an integrated circuit from digital engineering into which logic circuits can be programmed.

In a preferred embodiment of the method according to the invention, the sampling rate of the time signal of the transformed ultrasonic signal is 8 kHz. This bandwidth corresponds to the most sensitive audible range of human beings and is therefore easily perceptible. This bandwidth is sufficient for reproducing most physical technical and biological processes. Similarly, this bandwidth is sufficient to meet the requirements on reproducibility.

This embodiment of the method according to the invention performs frequency compression for the whole spectral content of the ultrasonic signal. The spectrum is not altered in qualitative terms, but the spectral resolution decreases by the compression factor. The temporal modification of an ultrasonic signal is maintained exactly even after application of the method according to the invention (preservation of the time profile of the signal dynamics). The frequency content of the ultrasonic signal is transformed into the audible range. It should be noted that frequency differences are not maintained but rather are likewise subject to scaling with the frequency factor. This may be disadvantageous when an ultrasonic signal is excited using active transmitters, since low modulation frequencies of a carrier signal (usually in the order of magnitude of approximately 1 kHz) are likewise scaled and, as a result, are perceived more poorly by the ear. This method is particularly useful when the ultrasonic signal is distributed over a wide frequency range and when spectral features exist. This is the case with almost all ultrasonic signals that are produced technically or biologically.

On the basis of the technological concept, the frequency compression was converted while retaining the temporal dynamic range in the form of a vocoder method. Since no high-resolution spectral lines are expected for the ultrasonic range in most cases, the method according to the invention is used, in one embodiment, not only for rendering ultrasonic signals audible but also for making considerable data compression for storage and further processing algorithms available. This affords great advantages, first of all, for the long-term observation of technical processes. The method according to the invention is used to achieve compression of the data up to a factor of 32 and therefore has a similar effect to MP3 compression. This has a positive effect on the effective use of memory space and computation power. Since, in contrast to the audio sector, there are no standard requirements concerning filter effects or edge effects (loss of information), there are no obstacles to the application of compression (besides the aim of rendering ultrasonic signals audible).

The data compression allows an effective reduction in the memory requirement. The method is loss-free particularly when the ultrasonic signal contains little information. This is the case in most naturally and technically produced ultrasonic signals.

Frequency shifts are already used technically. In the audio sector, for example, vocal ranges can be altered. A male voice can be turned into a female voice. Applications are in the entertainment industry, etc. These frequency shifts while preserving time modulation are relatively small, however (typically a factor of 1.5 . . . 2). Such small factors are not suitable for the transformation of ultrasonic signals. The application of the method according to the invention has surprisingly shown that a frequency shift for the ultrasonic signal up to a factor of 32 can be performed.

In a further embodiment of the method according to the invention,
an ultrasonic signal is digitally sampled,
1/n octaves are computed from the original signal by a filter bank,
a time-dependent level value is computed for each narrowband octave,
bandpass noise from the target frequencies is produced in the audible range, and
the acoustic signal obtained is output.

In this embodiment of the method according to the invention, the output of signals that contain only little information is used. In this case, the signal is broken down into frequency bands using filter banks. The frequency bands are then represented by an appropriate rms (root mean square) value.

The ultrasonic signal is digitally sampled, and subsequently 1/n octaves are computed from the original signal. That is to say that the original signal is broken down into frequency bands. This is accomplished by using a digital filter bank. For each narrowband octave, i.e. for each frequency band, a time-dependent level value or rms value is computed. This level value represents the amplitude of the ultrasonic signal in the respective frequency band.

For each frequency band, a scaled frequency band is defined, into which the ultrasonic information is scaled. For each frequency band, respective bandpass-limited noise is generated in the audible range. That is to say that the individual frequency bands are represented by narrowband noise. The noise is preferably computed by a digital noise generator in real time. This band noise is offset against the associated level value from the higher frequency band, and the correspondingly weighted noise is output. The simultaneous output of all narrowband noise signals then produces an aural impression of the wideband ultrasonic signal.

The intensity of the noise determines the volume that is output in this frequency range. In an embodiment of the method according to the invention, $\frac{1}{12}$ octaves are computed, that is to say that 27 noise sources generate an acoustic signal for transformed reproduction of a signal from 20-100 kHz, living up to the stochastic nature of ultrasonic signals in most cases in the aural impression.

In an embodiment of the method according to the invention, the frequency bands are scaled using a suitable factor. This scaling can be effected in linear or nonlinear fashion. Nonlinear scaling allows certain frequencies to be emphasized in the signal. As a result, alarm functions can be implemented in the method according to the invention when particular frequencies occur. The scaling using a suitable factor takes place prior to the multiplication by the level value.

In an embodiment of the present invention, the noise produced may be bandpass-limited white noise or pink noise.

This embodiment of the present invention likewise affords the advantage that storage of the signal requires a low memory capacity. The coefficients simultaneously also become useable for computing levels in frequency bands (important feature in machine diagnosis). The starting point and the filter width of the filter bank used can be adapted in a suitable manner for rendering the ultrasonic signals audible.

In a further embodiment of the method according to the invention, an overview of the whole ultrasonic spectrum is not necessary. Instead, details (e.g. modulations) are intended to be identified more accurately and the remaining frequencies masked out. Other methods are then used that shift the ultrasonic frequency band of interest to the audible range.

In a further embodiment of the method according to the invention,
the original time signal of the ultrasonic signal is registered,
a narrowband spectrum around a carrier frequency registers a narrowband signal,
the carrier frequency is automatically or manually varied, and
the narrowband signal is reproduced for each carrier frequency in the audible range.

The original time signal of the ultrasonic signal is registered. Around a carrier frequency, a narrowband signal is registered and assessed, the time modulation of the signal being maintained in the process. The relationship to the carrier frequency is lost. The frequency difference is maintained.

In an embodiment of the method according to the invention, no compression of the frequencies is necessary. The width of the signal band that is registered around the carrier frequency is likewise scaled. In an embodiment of the method according to the invention, a bandwidth of 4 kHz is produced for the output.

In a further embodiment, compression of the frequencies is performed e.g. when the modulations of interest comprise a swing >20 kHz. The method according to the invention can be modified such that the whole frequency range that the ultrasonic sensor registers can be assessed. In this embodiment, the rms values of the signals registered over a narrow bandwidth are a compressed representation of the original signal. The noise component that is needed to achieve a useable aural quality is produced synthetically and therefore requires no memory space.

The carrier frequency can be varied automatically or manually in the method according to the invention. The automatic sampling can produce a pseudo spectrum. The variation of the carrier frequency loses the temporal modulation of the signal to start with. Processing the stored original signal in accordance with the invention reproduces the narrowband signal for each carrier frequency by virtue of the original signal being repeatedly recomputed. For variable carrier frequencies it is then possible to reconstruct the temporal modulation of the signal.

In a preferred embodiment of the method according to the invention, the transformed signal is output substantially in real time via a suitable medium. A suitable medium may be a loudspeaker or headphones, for example. In a further preferred embodiment, the transformed signal is stored on a storage medium.

In an embodiment of the method according to the invention, an A-rating will be implemented in the signal chain. Since the assessment of the physical content of the ultrasonic signals is significant, it is necessary to take into consideration that, after frequency transformation and output in the audible range (headphones, loudspeakers), signals are subject to physiological and psychological assessment by the ear and the brain. The A-rating (DIN IEC 45631) takes this into consideration. In order to feel the real physical intensity of the signal, this attenuation or gain can be compensated for. One implementation variant consists in an inverse A-rating being implemented in the time signal of the output channel.

The invention is explained in more detail below with reference to 3 drawings.

Figure 1:
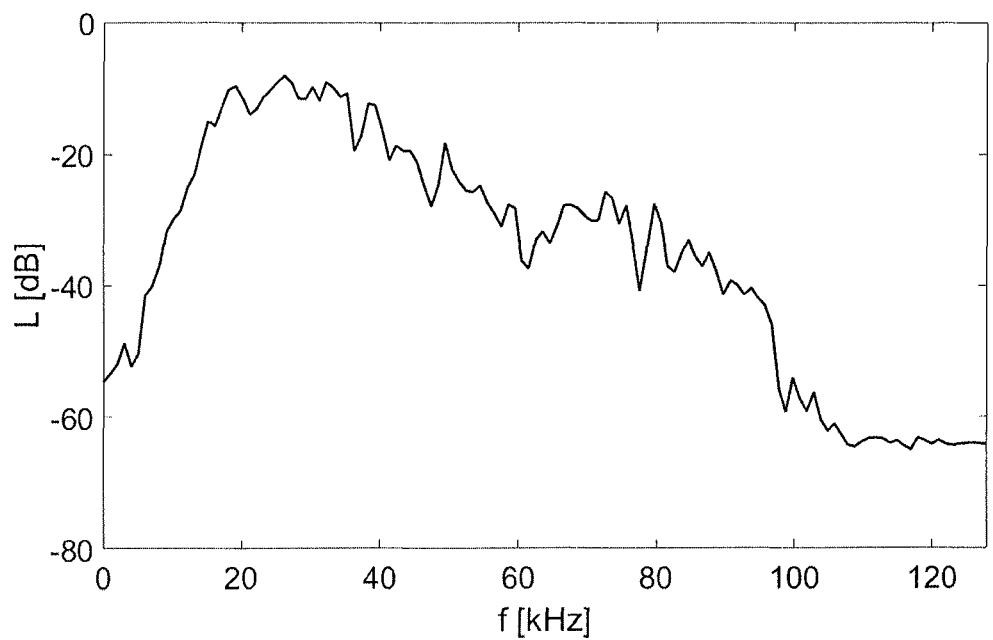
FIG. 1 shows a depiction of the power spectrum for application of the method using the Fourier transformation.
Figure 1:
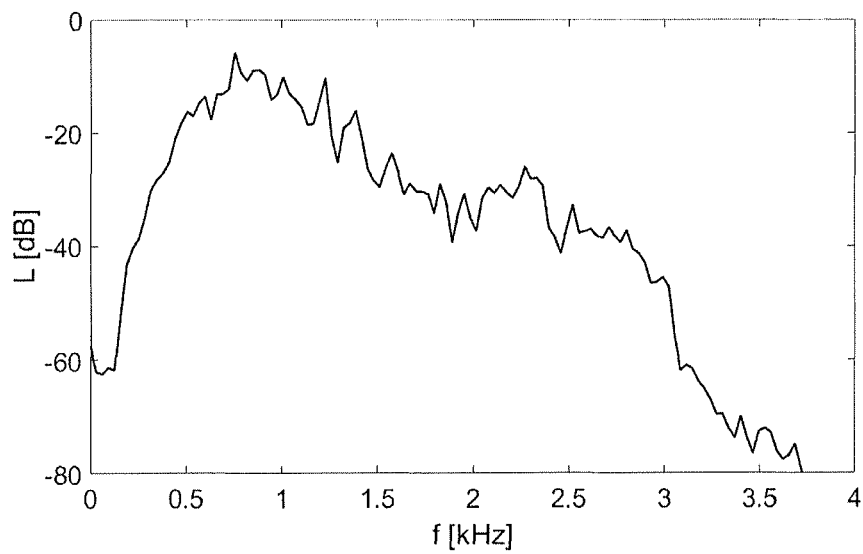
Figure 2:
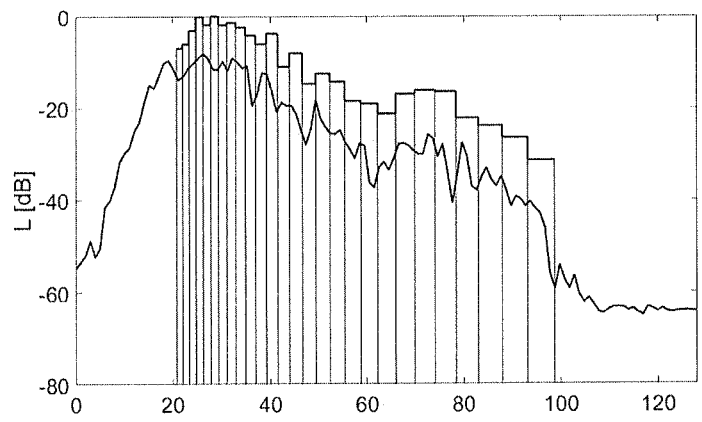
FIG. 2 shows a depiction of the power spectrum for application of the method using a filter bank.
Figure 2:
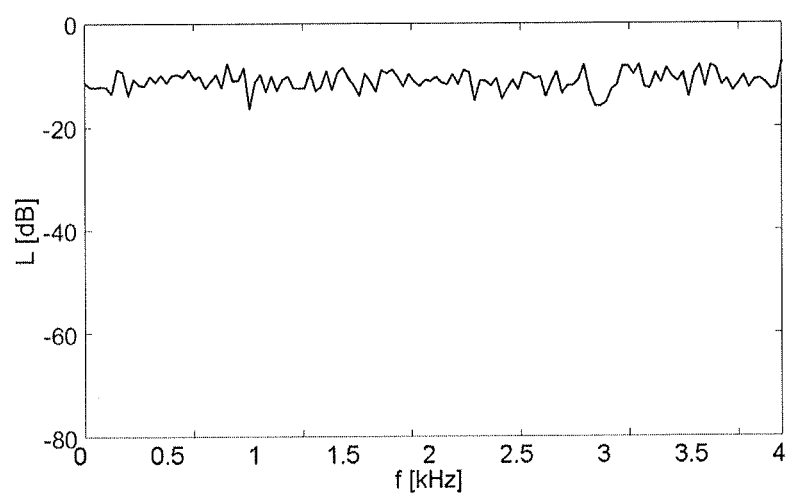
Figure 2:
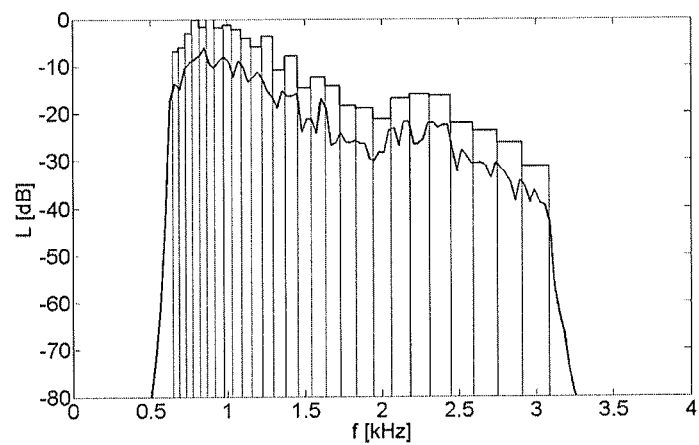
Figure 3:
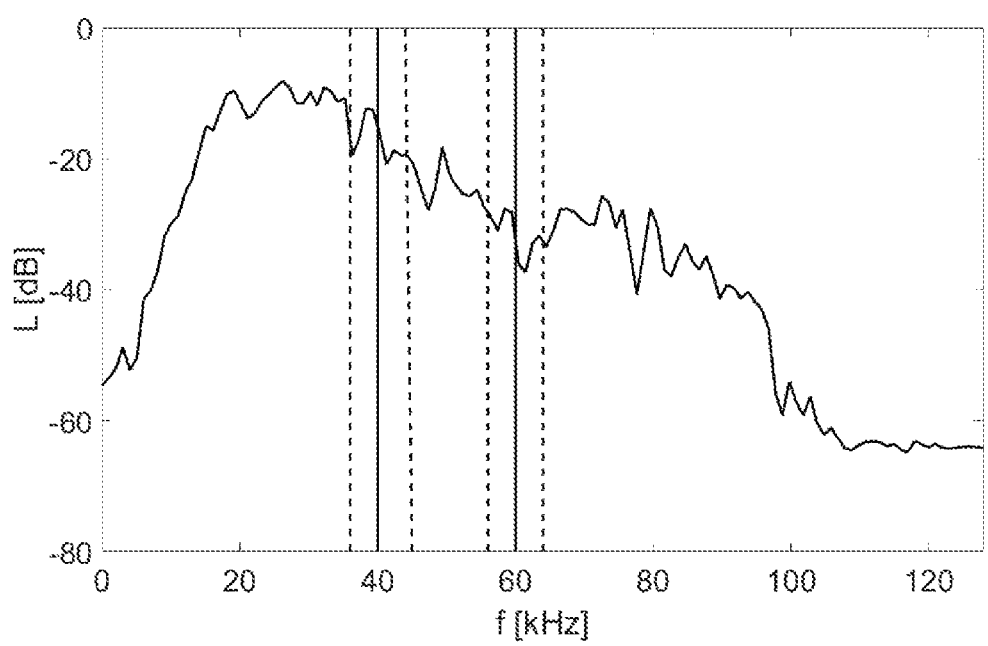
FIG. 3 shows a depiction of the power spectrum for application of the method using the evaluation of a narrowband signal range around a carrier frequency.
Figure 3:
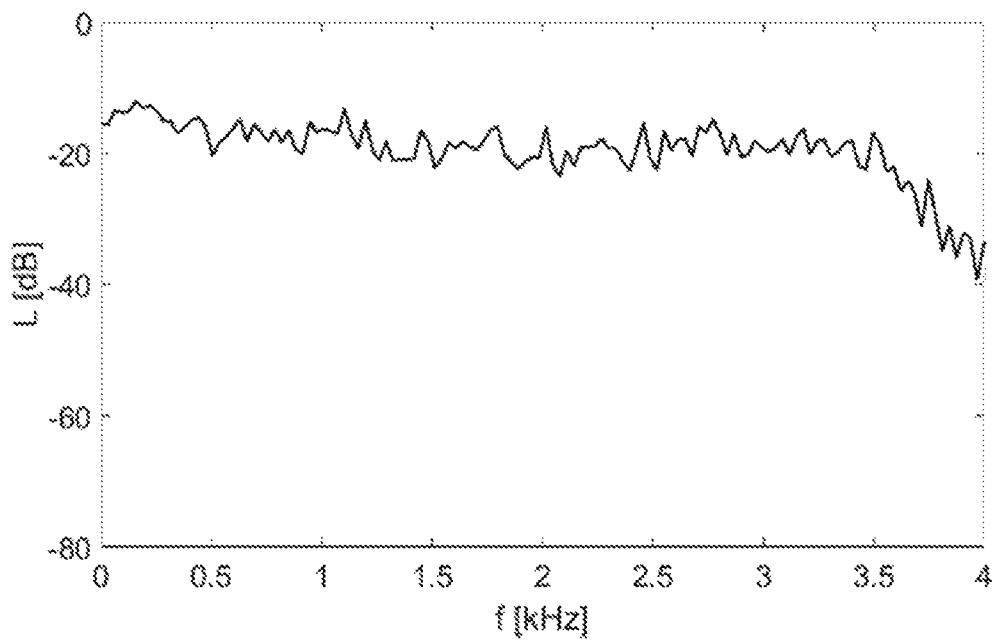
Figure 3:
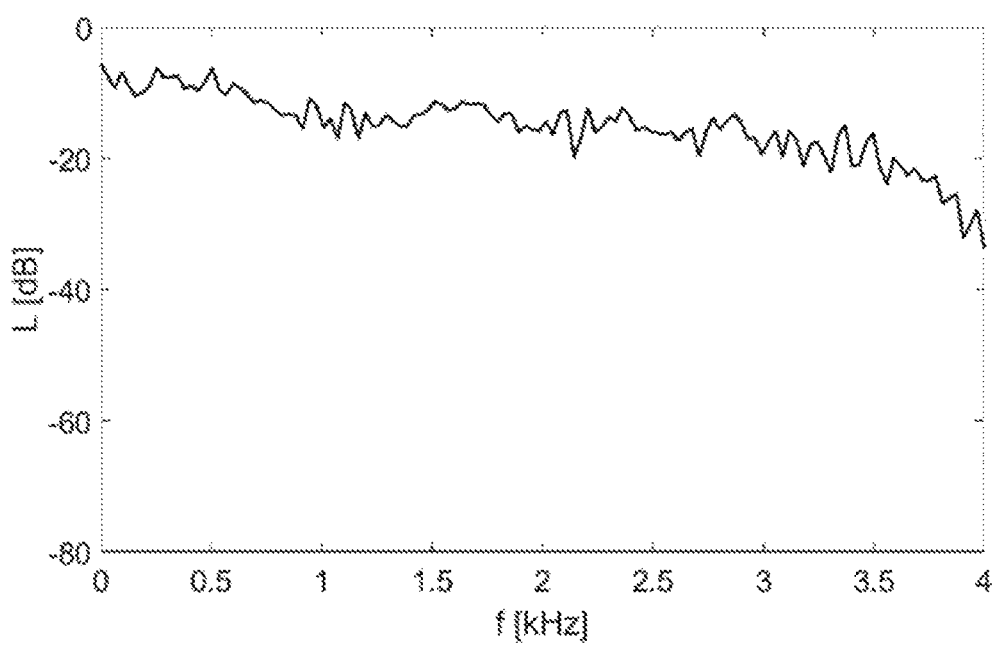

The sound pressure values in FIG. 1 to FIG. 3 are not referenced to 20 μPa. They are only relative indications of the sound pressure in dB.

The aspect of rendering ultrasonic signals audible relates to signals in the time domain. The illustration is provided in the frequency domain here, for reasons of better comprehensibility. The depiction in the frequency domain illustrates not only the aspect of rendering ultrasonic signals audible but also the requirement of data compression. The level values are not referenced to a reference value.

FIG. 1(a) shows the frequency spectrum (logarithmized representation of the power spectrum of a real ultrasonic signal produced by technical means). FIG. 1(b) depicts the spectrum that has been computed by means of vocoder methods and Fourier transformation. FIG. 2 shows the frequency spectrum (logarithmized representation of the power spectrum of a real ultrasonic signal produced by technical means) and the rms values of these bands, produced by means of a filter bank. FIG. 2(b) depicts the digitally produced noise curve that is used for the weighting with the intensities of the narrowband octaves. FIG. 2(c) shows the narrowband octave spectrum that is used for the output. The values represent the intensity of the signal to be rendered audible in the respective band that is used to weight the noise function.

FIG. 3(a) shows the frequency spectrum (logarithmized representation of the power spectrum of a real ultrasonic signal produced by technical means). Highlighting denotes that portion of the spectrum that is influenced by the mixing and that is available after the transformation for rendering the signal audible. In this method, the frequency axis is not scaled. Frequency differences are maintained. FIGS. 3(b) and 3(c) relate to the two mixed frequencies (40 and 60 kHz) and the different intensity, conditional thereon, of the respective output. The lower intensity in the range around 60 kHz in comparison with 40 kHz is also reflected in the spectrum of the down-converted signal.

The invention claimed is:

1. Method for rendering an ultrasonic signal audible while retaining a temporal dynamic range of the ultrasonic signal which method comprises
    digitally sampling a portion of an ultrasonic signal to obtain a digital signal sample;
    separating the digital signal sample into narrowband octaves using a digital filter bank;
    obtaining separate time-dependent amplitude level values for the digital signal sample within each of the narrowband octaves;
    defining a scaled frequency band for each of the narrowband octaves;
    generating in substantially real time a bandpass-limited noise signal in an audible range for each amplitude level value within each defined scaled frequency band; and
    outputting an audible noise signal for each narrowband octave within each defined scaled frequency band simultaneously.

2. Method according to claim 1, characterized in that the audible noise signals are output in real time.

3. Method according to claim 1, characterized in that the audible noise signals are output onto a storage medium.

4. Method according to claim 1, characterized in that an inverse A-rating is implemented in the audible noise signal.

5. The method according to claim 1 wherein each narrowband octave is a fraction of an octave band.

6. The method according to claim 1 wherein each narrowband octave is a 1/12 octave band.

7. The method according to claim 1 wherein the frequency band is defined by linear scaling.

8. The method according to claim 1 wherein the frequency band is defined by non-linear scaling.

* * * * *